United States Patent
Min et al.

(10) Patent No.: US 7,925,343 B1
(45) Date of Patent: Apr. 12, 2011

(54) SUBCUTANEOUS IMPLANTABLE CARDIAC DEVICE SYSTEM WITH LOW DEFIBRILLATION THRESHOLDS AND IMPROVED SENSING

(75) Inventors: Xiaoyi Min, Thousand Oaks, CA (US);
Scott Salys, Los Angeles, CA (US);
Yougandh Chitre, Valencia, CA (US);
Eric Falkenberg, Simi Valley, CA (US);
Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 620 days.

(21) Appl. No.: 11/539,576

(22) Filed: Oct. 6, 2006

(51) Int. Cl.
*A61N 1/39* (2006.01)

(52) U.S. Cl. .......................................................... 607/5

(58) Field of Classification Search .................. 607/4–5, 607/30–32, 129–131
See application file for complete search history.

(56) References Cited

U.S. PATENT DOCUMENTS

| | | | |
|---|---|---|---|
| RE30,372 E * | 8/1980 | Mirowski et al. ................. | 607/6 |
| 4,727,877 A | 3/1988 | Kallok | |
| 4,821,723 A | 4/1989 | Baker, Jr. et al. | |
| 4,932,407 A | 6/1990 | Williams | |
| 4,955,381 A | 9/1990 | Way et al. | |
| 5,014,696 A | 5/1991 | Mehra | |
| 5,020,544 A | 6/1991 | Dahl et al. | |
| 5,224,475 A | 7/1993 | Berg et al. | |
| 5,235,977 A | 8/1993 | Hirschberg et al. | |
| 5,247,945 A | 9/1993 | Heinze et al. | |
| 5,344,430 A | 9/1994 | Berg et al. | |
| 5,549,641 A | 8/1996 | Ayers et al. | |
| 6,076,014 A | 6/2000 | Alt | |
| 6,104,953 A | 8/2000 | Leyde | |
| 6,141,588 A | 10/2000 | Cox et al. | |
| 6,285,906 B1 | 9/2001 | Ben-Haim et al. | |
| 6,754,528 B2 * | 6/2004 | Bardy et al. ....................... | 607/5 |
| 2002/0183791 A1 * | 12/2002 | Denker et al. ..................... | 607/5 |
| 2003/0212436 A1 * | 11/2003 | Brown ............................... | 607/5 |
| 2005/0107834 A1 * | 5/2005 | Freeman et al. .................. | 607/5 |
| 2005/0115561 A1 | 6/2005 | Stahmann et al. | |
| 2005/0149138 A1 * | 7/2005 | Min et al. ......................... | 607/27 |

FOREIGN PATENT DOCUMENTS

| | | |
|---|---|---|
| EP | 0347353 A1 | 12/1989 |
| EP | 0588127 A1 | 3/1994 |
| GB | 2182566 A1 | 5/1987 |
| WO | 0222208 A2 | 3/2002 |
| WO | 0222208 A3 | 3/2002 |
| WO | 03039656 A1 | 5/2003 |
| WO | 2004047919 A2 | 6/2004 |

(Continued)

OTHER PUBLICATIONS

Unpublished U.S. Appl. No. 10/408,198, Knoll et al., available as prior art as of the publication of Min et al. on Jul. 7, 2005 which incorporates the application by reference.*

(Continued)

*Primary Examiner* — Scott M Getzow
*Assistant Examiner* — Amanda Patton

(57) ABSTRACT

A subcutaneous implantable cardiac device system applies defibrillation currents in pathways aligned with the heart's own electrical system to decrease defibrillation thresholds. In one implementation, one or more subcutaneous sensors detect ventricular fibrillation. Positioning of subcutaneous sensors and filtering result in improved sensing with reduced noise. A subcutaneous patch component of the system that is in communication with a subcutaneous pacemaker or cardioverter-defibrillator may perform the sensing and apply the defibrillation. The subcutaneous patch may include one or more electrodes that perform both sensing and defibrillation. Variations of the subcutaneous patch may include battery and capacitor for generating onboard defibrillation current and may also include a microprocessor for advanced programmable operation.

16 Claims, 11 Drawing Sheets

FOREIGN PATENT DOCUMENTS

WO 2004047919 A3 6/2004
WO WO 2005107864 A1 * 11/2005

OTHER PUBLICATIONS

NonFinal Office Action, mailed Oct. 28, 2008: Related U.S. Appl. No. 11/539,584.
Final Office Action, mailed Apr. 9, 2009: Related U.S. Appl. No. 11/539,584.
NonFinal Office Action, mailed Sep. 28, 2009: Related U.S. Appl. No. 11/539,584.
NonFinal Office Action, mailed May 18, 2010: Related U.S. Appl. No. 11/539,584.

* cited by examiner

SUBCUTANEOUS IMPLANTABLE CARDIAC DEVICE SYSTEM WITH LOW DEFIBRILLATION THRESHOLDS AND IMPROVED SENSING

CROSS-REFERENCE TO RELATED APPLICATIONS

This application is related to U.S. patent application Ser. No. 11/539,584, filed concurrently herewith, titled "Subcutaneous Implantable Cardiac Device System with Low Defibrillation Thresholds and Satellite Ventricular Pacer".

TECHNICAL FIELD

Subject matter presented herein generally relates to implantable medical devices and more particularly to a subcutaneous implantable cardiac device system with low defibrillation thresholds and improved sensing.

BACKGROUND

Implanted devices provide therapy for many kinds of cardiac problems. Their effectiveness results from precise sensing of the electrical waveforms generated by the heart during ongoing cardiac cycles and precise application of remedial electrical pulses in a manner that conserves an onboard battery for many years.

Implanted devices have conventionally relied on relatively invasive installation procedures to attain the precision needed for effective cardiac control while simultaneously sparing the implanted battery. That is, in order to be practical, conventional electrodes are meticulously positioned—often across heart valves—to be in contact with cardiac tissue in the most inviolate recesses of the heart. Fortunately, this cardiac invasiveness has proven to be relatively safe. Implanted cardiac leads are now taken for granted. Still, problems can arise after electrode placement, and lead placement inside the heart is avoided if there is a workable alternative.

Another problem with conventional lead placement for implanted cardiac devices is the level of skill and sophistication of equipment needed to achieve good placement. An implantation procedure typically lasts a couple of hours and requires a small team of skilled practitioners threading leads transvenously under the assistance of x-ray fluoroscopy. In other words, conventional lead placement is relatively expensive. Nonetheless, this expensive procedure is currently the standard and the resulting conventional implanted cardiac devices successfully treat many cardiac ailments.

Perhaps the gravest of these cardiac ailments is ventricular fibrillation. The condition is so serious that it sometimes goes by other names, such as "cardiac death" and even "sudden cardiac death." In ventricular fibrillation, the heart rate in the ventricles becomes ineffectively rapid because the electrical activity controlling the ventricles has become completely chaotic. The heart beats so quickly and chaotically that the ventricles effectively tremble instead of pumping blood. An implanted cardiac device can be programmed to respond to ventricular fibrillation by applying a strong electrical shock that stops all erratic electrical activity allowing a normal cardiac rhythm to ensue.

A similar malady, ventricular tachycardia, occurs when the electrical impulses controlling the ventricles remain orderly but occur far too rapidly to effectively pump blood. Ventricular tachycardia can quickly turn into ventricular fibrillation. Conventional implanted cardiac devices can treat ventricular tachycardia. If ventricular tachycardia is sensed, an implanted device can apply rapidly paced beats—anti-tachycardia pacing—at a pace that is even more rapid than the tachycardia, thereby overcoming the heart's own abnormal rate. When the artificial pacing is stopped, the heart often returns to a normal rate and rhythm. Sometimes anti-tachycardia pacing does not work, so a second tier remedy is applied in the form of cardioversion shocks that are timed to coincide with features of the heart's inherent rhythm in order to stop the ventricular tachycardia and bring the rate and rhythm back within normal parameters.

To achieve the advantages of a conventional implantable cardioverter-defibrillator (ICD) as just described but avoid invasive and expensive installation of the ICD, various conventional systems have been attempted that utilize subcutaneous components. A subcutaneous ICD system aims to have electrodes that do not physically invade the heart to theoretically provide the best of both worlds: defibrillation capability with relatively quick and easy installation of the device. But in practice, such conventional subcutaneous or semi-subcutaneous systems have suffered several drawbacks. First, since the electrode for originating a defibrillation current is not in physical contact with the heart, more current is needed to perform defibrillation, i.e., these systems result in a higher "defibrillation threshold"—which is harder on the patient and on the battery when defibrillation is applied.

Second, conventional subcutaneous installations result in a positioning of electrodes that is at variance with optimal electrode locations for sensing and stimulating the heart—e.g., the shocking pathway(s) achieved impinge the heart in non-optimal planes. This increases defibrillation thresholds.

Third, to keep the system subcutaneous and noninvasive, the sensing electrodes, like the shocking electrodes, are also not in physical contact with the heart. Thus, sensing is more difficult and prone to noise interference.

There is a need for subcutaneous and semi-subcutaneous implantable systems that enable defibrillation thresholds that are comparable to those of conventional ICDs while also providing improved sensing.

SUMMARY

A subcutaneous implantable cardiac device system applies defibrillation in a manner that decreases defibrillation thresholds. In one implementation, one or more subcutaneous sensors detect ventricular fibrillation. Positioning of subcutaneous sensors and filtering result in improved sensing with reduced noise. A subcutaneous patch component of the system that is in communication with a subcutaneous pacemaker or cardioverter-defibrillator may perform the sensing and apply the defibrillation. The subcutaneous patch may include an electrode that performs both sensing and defibrillation. Variations of the subcutaneous patch may include battery and capacitor for generating onboard defibrillation current and may also include a microprocessor for advanced programmable operation.

DETAILED DESCRIPTION

Overview

Figure 1A:
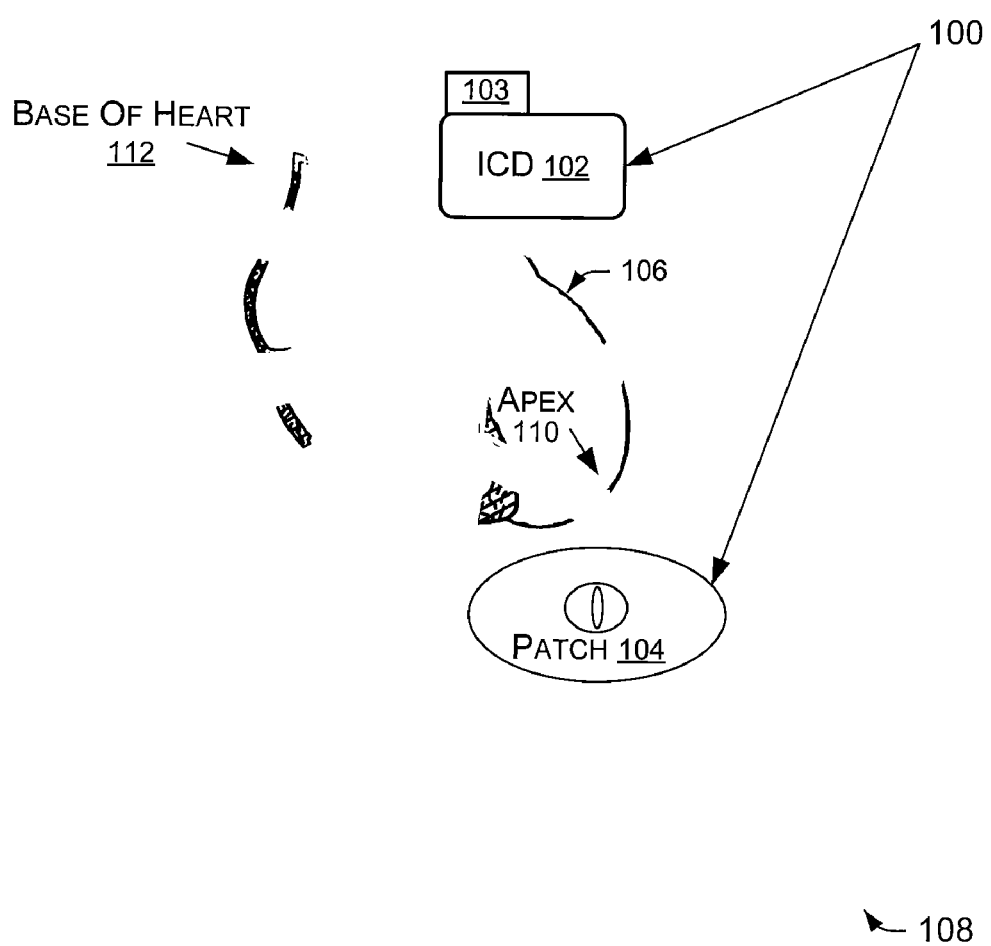
FIG. 1a is a diagram illustrating an exemplary subcutaneous system for applying defibrillation at a reduced defibrillation threshold, including a subcutaneous patch.

The following discussion describes exemplary subcutaneous implantable cardiac device systems that achieve lower defibrillation thresholds and improved sensing over conventional subcutaneous systems. In one implementation, such an exemplary subcutaneous system includes an implantable cardiac device, such as an implantable cardioverter-defibrillator (ICD), in communication with one or more subcutaneous electrodes off board the ICD that can be implemented in various forms, such as a remote coil electrode array, a remote patch electrode ("patch electrode"), or a remote multifunction patch array ("patch array"). For the sake of clarity in the description, each of these various types of subcutaneous electrodes—patch electrode, patch array, and coil electrode—will be referred to generically herein as a "patch." In a typical arrangement, an exemplary patch is an electrode or a capacitor-electrode combination that can deliver a shocking pulse. A wire between the ICD and the patch allows current transfer between electrodes that are placed to define efficient electrical pathways across the heart. An exemplary patch may perform both sensing and shocking functions and even additional functions.

Among the various ways that an exemplary system provides a lower defibrillation threshold and improved sensing over conventional subcutaneous systems are electrode geometry, configuration, and placement. These features of systems described herein enable access to more efficient electrical pathways ("vectors") for sensing and shocking than can be accessed by conventional subcutaneous systems. That is, an exemplary system can establish more efficient sensing, pacing, and shocking vectors than conventional subcutaneous systems.

When an exemplary patch is to be used for defibrillation, then in various implementations, communication and energy transfer between the ICD and the patch use a communication wire. In some implementations, one or more sensors can also be added along such a communication wire. These sensors may be integrated into the system to increase the sensitivity of sensing functions and provide earlier confirmation of conditions, such as ventricular fibrillation.

Sensors on the ICD, sensors on the patch, and sensors positioned along the communication wire can also be logically or electrically conjoined to form an electrode array for gathering ECG readings. Depending on a specific configuration of electrodes available in an exemplary system, electronic elements in the ICD and/or the patch can intelligently select which electrodes to include in an electrode array for measuring an ECG, and can switch electrode combinations to achieve an optimized ECG array for a given person or circumstance.

A patch electrode or patch array can be implemented at various levels of complexity depending on system configuration to more effectively sense, pace, and shock than conventional subcutaneous devices. For example, in one implementation, a patch has a surface geometry that lowers defibrillation thresholds. In other implementations, a patch has onboard programmability and/or carries out onboard decision-making.

Exemplary System

FIG. 1a shows one implementation of an exemplary implantable subcutaneous system 100, including an ICD 102 and a patch 104 that are situated in relation to a human heart 106, a rib cage 108, and in relation to each other. In the shown implementation, the ICD 102 is implanted in a subcutaneous location in the left pectoral region, and the patch 104 is implanted in a subcutaneous location over (superficial to or anteriorly located over) the apex 110 of the heart 106 in a transverse plane that is inferior to the apex 110 of the heart and in a saggital (or medial) plane that may be lateral to the apex 110 of the heart. These subcutaneous locations of the ICD 102 and patch 104 can be varied, of course. Descriptions of component locations assume a human body in standard anatomical position.

Figure 1B:
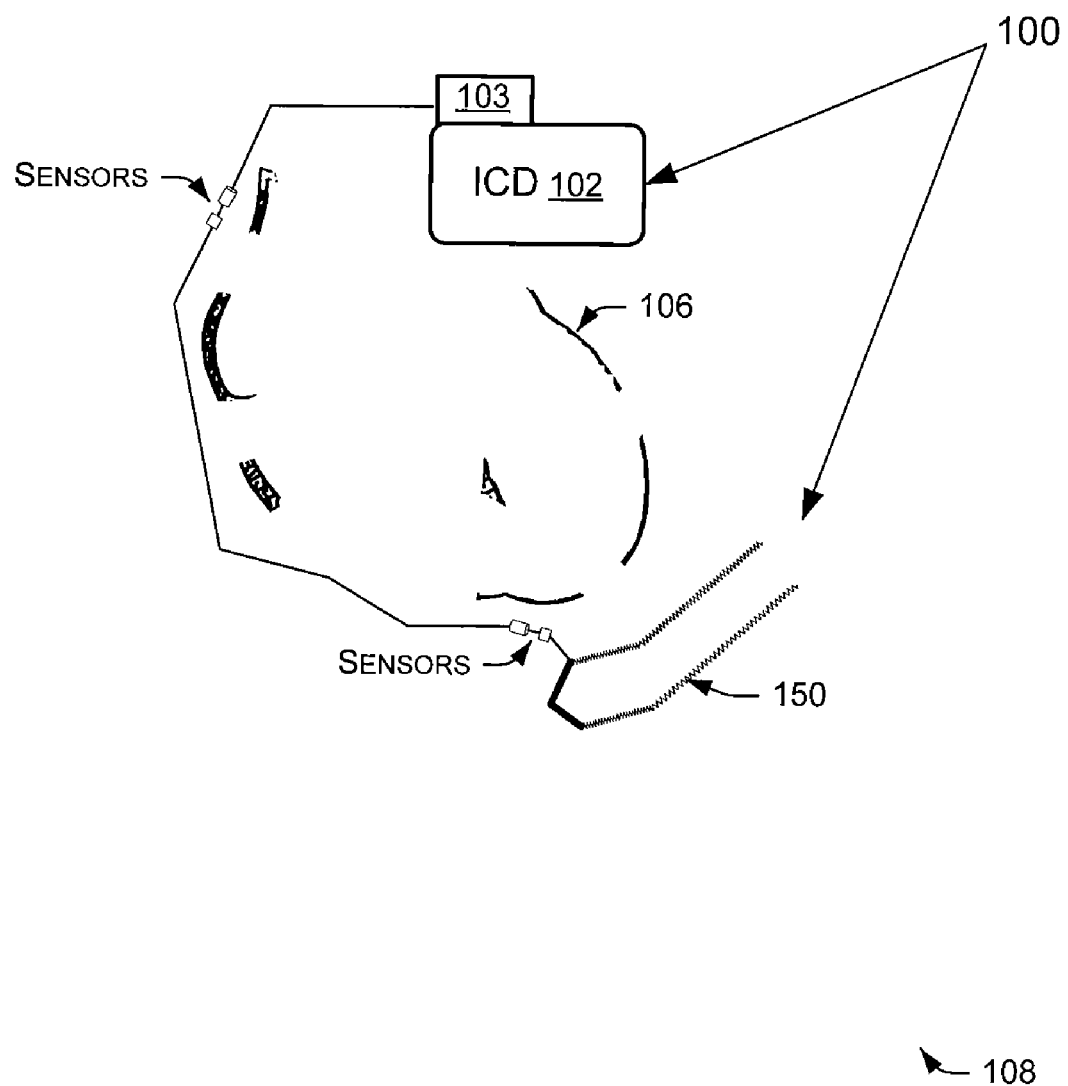
FIG. 1b is a diagram illustrating an exemplary subcutaneous system for applying defibrillation at a reduced defibrillation threshold, including a subcutaneous coil electrode array.

FIG. 1b shows a similar exemplary configuration, except that one or more subcutaneous coil electrodes 150 are substituted for the patch 104 of FIG. 1a. Both the patch 104 of FIG. 1a and the coil electrodes 150 of FIG. 1b can be implanted or inserted with minimal invasiveness and can provide an electrode that offers a greater surface area for originating defibrillation shocks than a conventional transvenous electrode. Although a patch 104 may include components for wireless communication with the ICD 102, a coil electrode 150 assumes a communication wire with an ICD 102, to be described more fully below. A patch 104 is also likely to be coupled with the ICD 102 via a wire for at least transfer of shocking energy if the patch delivers defibrillation shocks, but this does not preclude wireless communication between the patch 104 and the ICD 102.

"Subcutaneous," as used here, means that most or all of the components of a system 100—especially sensors and leads as well as the ICD 102, patch 104 or coil electrodes 150, etc.—are beneath the skin yet superficial to layers of skeletal muscle tissue, rib bones, and costal cartilage, and therefore relatively easily installed with minimal invasiveness. The term "subcutaneous" will be used somewhat loosely herein because some implementations of an exemplary subcutaneous system 100 may have no physical contact with cardiac tissue (a "no-touch" system) while other implementations of an exemplary subcutaneous system 100 may have minimal contact with cardiac tissue (a "minimal-touch" system). For example, in one implementation an electrode that contacts cardiac tissue may be used (shown in FIG. 4). So, the term "subcutaneous" is selected and used herein to distinguish the subject matter from conventional "non-subcutaneous" ICD systems in which most or all of the electrodes contact cardiac tissue. In the exemplary subcutaneous systems described herein, most or all of the electrodes do not contact cardiac tissue. Often, if an exemplary electrode that contacts cardiac tissue is used, the electrode only contacts the heart epicardially—on the outside surface of the heart—for minimal invasiveness.

"Defibrillation threshold" is a term of art for the lowest practical shock energy that achieves defibrillation. Generally, the less elegant the method of conventional shock delivery, the greater the energy required for effective defibrillation. For example, externally applied currents through cardiac arrest "paddles" transfer a great deal of energy to achieve defibrillation, for example 150 Joules. The low defibrillation thresholds enabled by the exemplary systems 100 described herein provide the elegance of less painful and intrusive shocks to a human patient while preserving the battery life of components in the exemplary system 100, which can also be made smaller and can provide better safety margins.

Among the various ways that an exemplary system 100 provides a lower defibrillation threshold than conventional subcutaneous systems are electrode geometry, configuration, and placement, as mentioned. In some implementations of the subject matter, placement of electrodes is also responsible for improved sensing. The improved sensing, in turn, may also be responsible for providing a lower defibrillation threshold in some circumstances. These electrode characteristics can create or provide access to electrical vectors that enable the lower defibrillation thresholds and improved sensing.

Shocking Vectors

Figure 2:
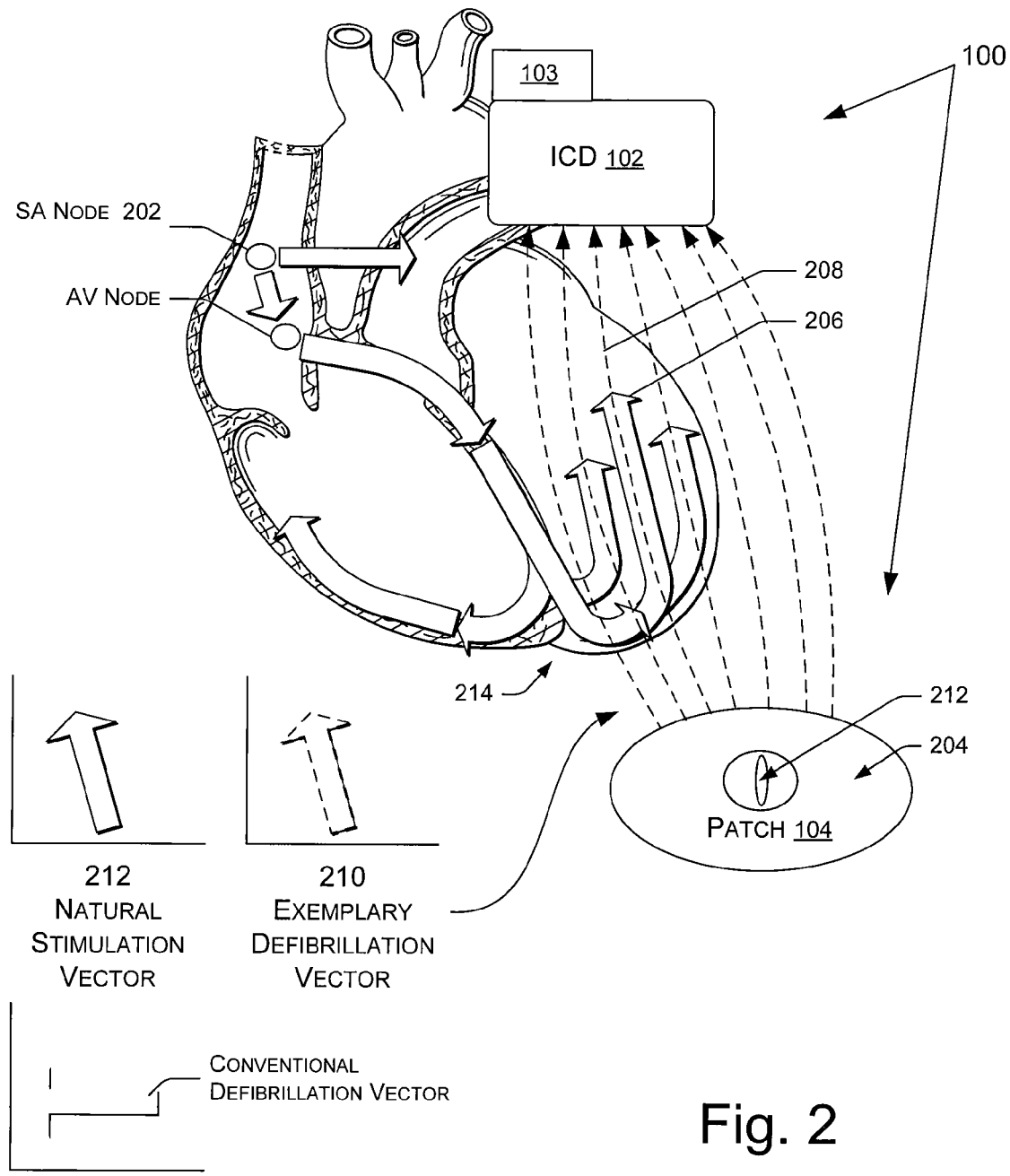
FIG. 2 is a diagram illustrating exemplary placement of subcutaneous electrodes to decrease a defibrillation threshold.

FIG. 2 shows example electrical vectors established by components of an exemplary implantable subcutaneous system 100. The illustrated configuration achieves lowered defibrillation thresholds comparable to those of a conventional non-subcutaneous ICD system that uses a right-ventricular-lead to case-electrode circuit for delivering defibrillation shocks.

The illustrated system 100 includes an ICD 102, which may have various electrodes on its exterior (including the case itself), and a patch 104, which may have more than one electrode available. For example, part of a patch 104, i.e., a conductive electrode 204, may be made of a conductive mesh for applying defibrillation shocks while another part of the patch acts as a sensor (e.g., 212). Thus, combinations of electrodes available in association with these two components, the ICD 102 and the patch 104, provide the possibility of establishing various electrical vectors for sensing and affecting a cardiac electrical system. Depending on the physical placement of the ICD 102 and the patch 104—in relation to each other within the thoracic cavity and in relation to a patient's heart—many electrical vectors are accessible for providing cardiac sensing and therapy, such as, pacing, cardioverting, and defibrillating; with increased sensitivity of sensing and lowered defibrillation thresholds.

In the illustrated system 100 of FIG. 2, the increased efficiency over conventional subcutaneous systems may be due to combinations of electrode characteristics and placement factors. First, the ICD 102 and patch 104 may be placed so that a circuit formed by current flow between them aligns with natural electrical pathways 206 of the heart 106 (e.g., conduction fibers). This may result in a more efficient use of energy with lower thresholds for achieving a desired cardiac response. For example, when the illustrated patch electrode 204 sends a defibrillation current to a case electrode of the ICD 102, the defibrillation current pathways 208 align with the heart's own myocardial depolarization wave pathways 206 that are normally present during ventricular stimulation by the heart's electrical system. Thus, a defibrillation current vector 210 established by the exemplary system 100 reinforces a vector 212 representing the heart's own ventricular stimulation during normal systole.

Second, the location of an exemplary electrode may be proximal to a relevant area of electrical activity on the heart 106, such as the sinoatrial node 202. For example, an electrode 204 associated with a patch 104 may be placed subcutaneously over the apex 110 of the heart 106 to more effectively stimulate an area 214 where a wave of myocardial cell depolarizations spread from a nexus of Purkinje fibers (myocardial conduction fibers) in the septum of the heart to begin propagation across the ventricles. In other words, since the apex 110 of the heart 106 is the heart's own region for originating stimulation of the ventricles, it makes sense to originate a defibrillation shock in the same area (this also saves electricity, which is at a premium in a battery operated device).

Third, a host of other factors may favor the efficacy of an exemplary electrode 204, including composition, geometry, and/or placement, as mentioned above. As one example, depending on its placement, a patch electrode 204 that has a relatively large surface area may be able to originate a more pervasive wave of stimulation in a ventricle than a small conventional electrode. Additionally, an exemplary subcutaneous electrode 204 with a relatively large surface area may have increased chances of taking advantage of higher electrical conductivity of certain body tissues along a given vector—i.e., may have greater chances of finding a path of least resistance that stimulates the heart, thereby lowering the defibrillation threshold.

Figure 3:
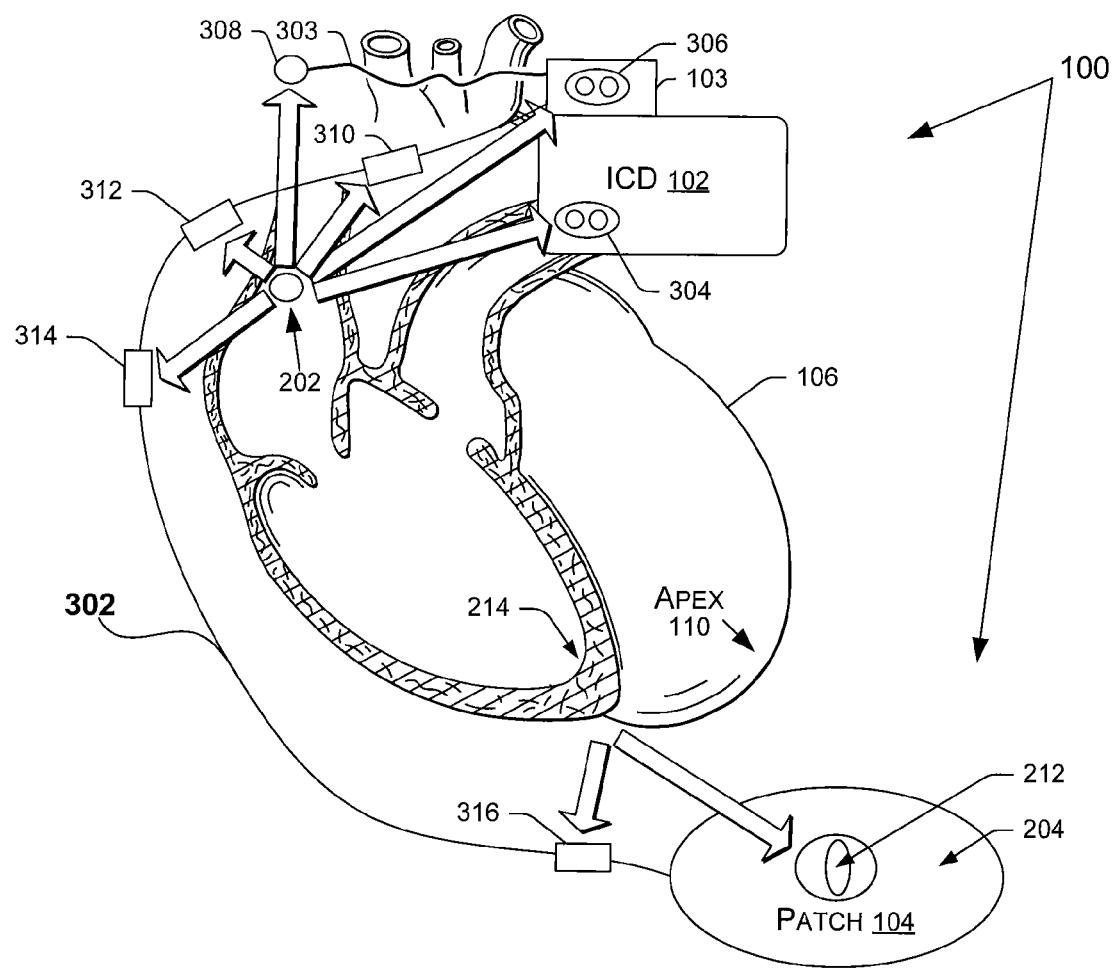
FIG. 3 is diagram illustrating exemplary placement of subcutaneous sensors for improved sensing.

FIG. 3 shows an exemplary system in which a communication wire 302 couples the ICD 102 with an exemplary patch 104. If a patch 104 is to be used for defibrillation, then in various implementations, data exchange and/or energy transfer between the ICD 102 and the patch 104 is communicated over the communication wire 302, which may be a thin, flexible, conducting cable to at least set up a shocking circuit. This, however, does not preclude wireless communication between an ICD 102 and a patch 104. Thus, the ICD 102 may have an antenna 303 for wireless communication. The communication wire 302 may be implanted by subcutaneously tunneling between a subcutaneous ICD 102 and a subcutaneous patch 104.

A communication wire 302 is even more likely to be used when a patch 104 implementation is "stripped-down" to little more than a mesh electrode 204 or a coil electrode array 150. On the other hand, a patch 104 may be a nearly "self-contained", depending on intended functionality. In the latter case, even if a patch 104 has a substantial onboard battery and capacitor capable of generating defibrillation pulses, the patch 104 may still include a communication wire 302 to exchange data with the ICD 102 or enable a circuit that sends defibrillation energy to, through, and around the heart. In one implementation, a patch 104 communicates with the ICD 102 in a wireless manner but deploys a remote subcutaneous electrode of its own (not illustrated) via a wire that is not connected to the ICD 102.

The communication wire 302 may also be used to link one or more "proximal" sensing electrodes (e.g., 304, 306, 308, 310) situated along its length to the ICD 102, to the patch 104, or to both. Thus, the wire 302 may be used for multiple functions, such as communication between the ICD 102 and patch 104; communication with sensors disposed along the wire 302; creating a circuit for transferring shocking energy for defibrillation; etc. A given exemplary system 100 may have fewer sensing electrodes than the number of sensors illustrated in FIG. 3 to show potential locations. But an exemplary system 100 could have the illustrated number of sensing electrodes and even more, but perhaps not use all of the sensors at any one time.

Sensing Vectors

A sensing electrode is referred to as "proximal" if it is relatively near a special electrical feature of the heart or in contact with cardiac tissue. A proximal electrode may be situated at advantageous locations in the system 100, such as on the ICD 102 (e.g., sensor 304), along the wire 302 (e.g., sensors 310, 312, 314, 316), and/or on the patch 104 (e.g., sensor 212). For example, a given proximal sensing electrode 304 may be coupled with the ICD 102 and positioned near an electrically energetic part of one of the atria, for example, near a relevant feature such as the sinoatrial node 202, atrioventricular node, or other location of favorable reception of the heart's own electrical activity. A proximal sensing electrode is characterized by reliable, low-noise sensing but can be positioned in a variety of locations, including endocardially, epicardially, pericardially, transvenously, or along the aforementioned communication wire 302. For an exemplary subcutaneous system 100, one goal is to strike a balance between having a proximal sensing electrode that is non-invasive to the heart while providing a good sensing performance.

A proximal sensing electrode (e.g., 212) in a patch 104 placed at level inferior to the apex 110 of the heart 106 may be integrated into the system to sense ventricular rhythms and events. It should be noted that location of a proximal sensing electrode is typically selected for minimum invasiveness in keeping with the subcutaneous character of the subject matter.

A proximal sensing electrode may be used, for example, to increase the precision and sensitivity of sensing cardiac events and abnormalities; and more specifically to precisely confirm or give an early warning of ventricular fibrillation. A proximal sensing electrode often achieves the improved sensing because its proximity to electrically active features of the heart allows it to overcome noise from electromagnetic interference (EMI), depolarizing action potentials of myocardial cells, etc. Incorporation of one or more proximal sensing electrodes may provide an earlier identification (or confirmation) of arrhythmias or fibrillation than conventional subcutaneous techniques—sometimes allowing a lower energy shocking response rather than a maximum power response to fibrillation.

The various sensing electrodes illustrated in FIG. 3 can be integrated into an exemplary "no-touch" subcutaneous system 100 that does not contact cardiac tissue in order to provide increased sensitivity of sensing and provide early confirmation of ventricular fibrillation that is comparable to the sensing of non-subcutaneous conventional systems.

Figure 4:
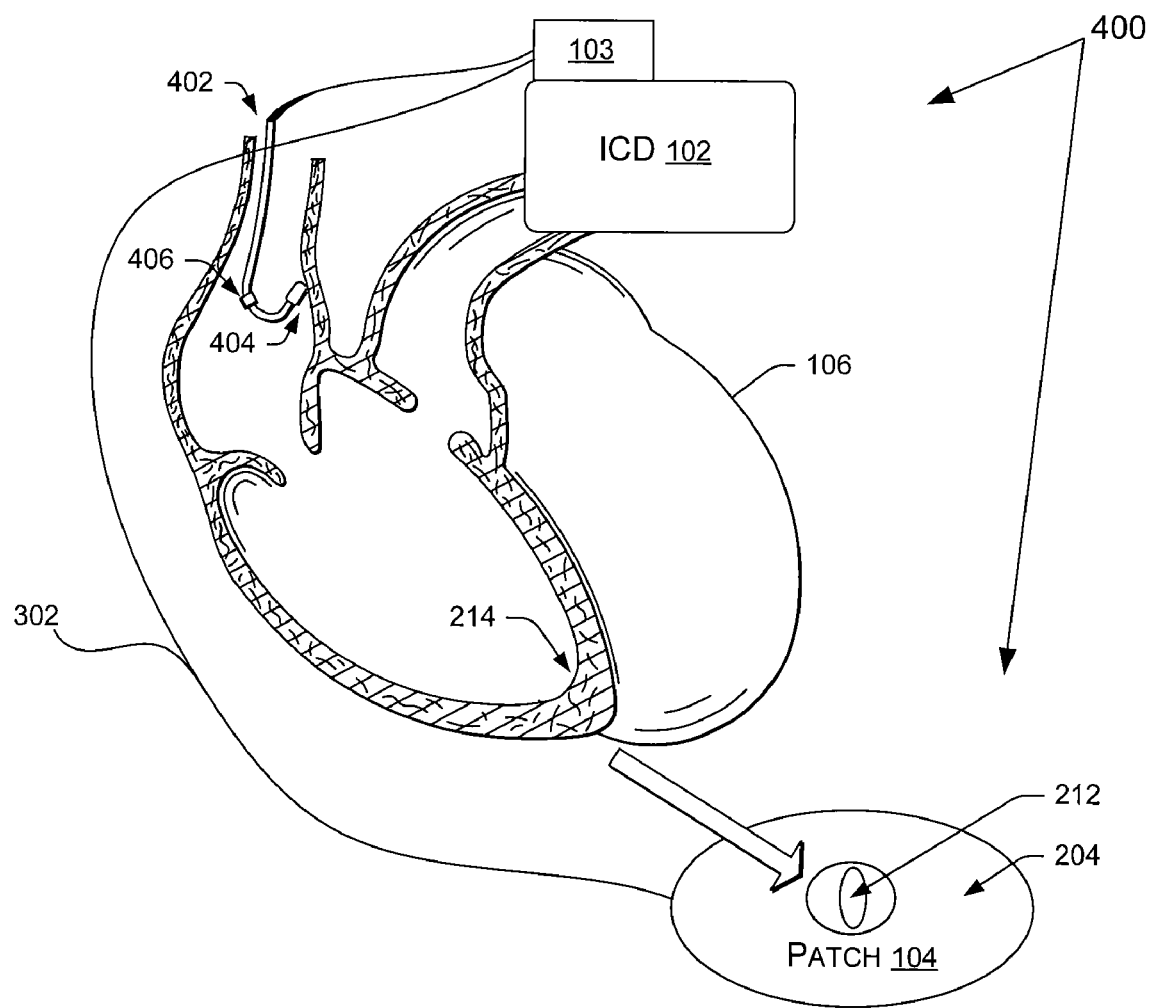
FIG. 4 is a diagram illustrating confirmation of ventricular fibrillation using a right atrial lead.

As shown in FIG. 4, in another aspect of the subject matter, an exemplary system 400 includes a proximal sensing electrode, in this case a right atrial lead 402, that is coupled with the ICD 102 and is in contact with cardiac tissue. A proximal sensing electrode such as the right atrial lead 402 may be used instead of or in addition to sensing electrodes positioned along a communication wire 302. Such a proximal sensing electrode that contacts cardiac tissue aims to provide reliable sensing and confirmation of ventricular fibrillation just like proximal sensing electrodes (e.g., 304) that do not contact cardiac tissue. A configuration that includes a proximal sensing electrode, such as the right atrial lead 402 in contact with cardiac tissue, may be deliberately implemented or may result when an exemplary subcutaneous patch 104 is retrofitted into a pre-existing pacemaker or ICD setup that already has a lead in place that can function as a proximal sensing electrode. In the latter circumstance, there may be no reason to not use the pre-placed electrode, and the additional subcutaneous components that make up the exemplary system 400 can still be placed with minimal invasiveness. A proximal sensing electrode can make an early determination of ventricular fibrillation that is followed by a defibrillation shock applied through the patch 104. Such an exemplary system 400 is typically also capable of pacing a slow heart rate and providing anti-tachycardia pacing and cardioversion for ventricular tachycardia.

If a right atrial lead 402 is used as a proximal sensing electrode, then the right atrial lead 402 may support an atrial tip electrode 404, which is typically implanted in a patient's right atrial appendage. The right atrial lead 402 may also support a right atrial ring electrode 406, which enables the device to sense atrial cardiac signals and apply pacing therapy to the right atrial chamber.

A right atrial lead 402 is described as one example of a cardiac lead that could be used as a proximal sensor and for pacing, because it provides minimal invasiveness compared with other leads such as ventricular leads and coronary sinus leads. However, these and other leads could be used too, such as a right ventricular lead (not shown) electrically coupled to a right ventricular tip electrode, a right ventricular ring electrode, a right ventricular (RV) coil electrode, a superior vena cava (SVC) coil electrode, etc. Typically, a right ventricular lead is transvenously inserted into the heart 106 to place the right ventricular tip electrode in the right ventricular apex so that the RV coil electrode is positioned in the right ventricle and the SVC coil electrode is positioned in the superior vena cava. Accordingly, a right ventricular lead is capable of receiving cardiac signals, and delivering stimulation in the form of pacing to the right ventricle.

As shown in FIGS. 5-8, an exemplary patch can have various implementations at different levels of complexity in which its electrodes more effectively sense, pace, and/or shock than conventional subcutaneous devices, including implementations in which the patch's functionality has onboard programmability and/or implementations in which an intelligent patch carries out onboard decision-making.

Figure 5:
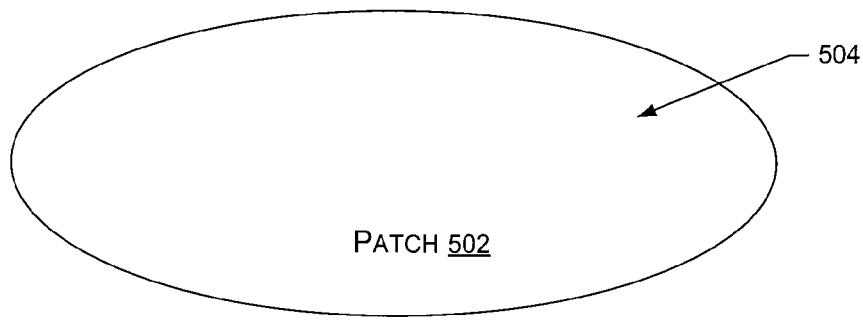
FIG. 5 is a diagram illustrating an exemplary single electrode subcutaneous patch.

FIG. 5 shows an exemplary patch 502 including an electrode 504 that delivers defibrillation shocking. The electrode 504 may be constructed of conductive material, such as metal, metallic conductive polymer, metallic mesh, multi-looped coils, etc. The shown patch 502 delivers defibrillation shocks without being in physical contact with the heart.

In a variation, the patch 502 is a single physical electrode, as above, but has two electrical or logical functions. The patch 502 acts as a unipolar sensor relative to the exterior case of an ICD 102, detecting QRS wave features for determining onset of ventricular tachycardia or ventricular fibrillation, and then functions as an electrode (relative to an exterior case electrode of the ICD 102) for delivering anti-tachycardia pacing, cardioversion, or defibrillations shocks. In this implementation, switching between sensing and shocking functions can be controlled by an ICD 102.

Figure 6:
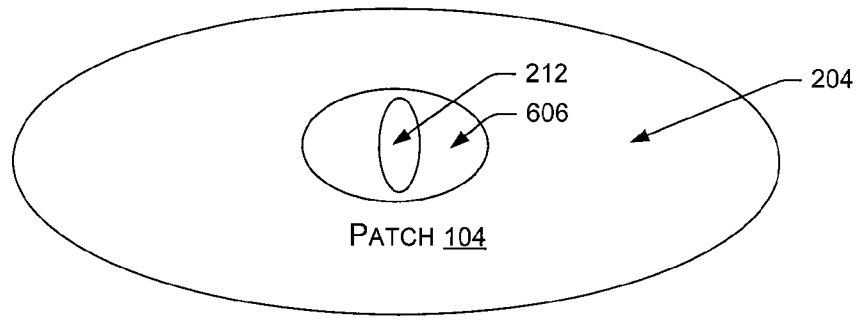
FIG. 6 is a diagram illustrating an exemplary dual electrode subcutaneous patch.

FIG. 6 shows another implementation of an exemplary patch 104. The illustrated patch 104 has physical characteristics similar to the patch 502 shown in FIG. 5, that is, a relatively large electrode 204, but has additional features of an electrical insulator region 606 surmounted by a second conductor 212, thereby forming two electrodes. In one implementation, the large electrode 204 of the patch 104 may act as a cathode for defibrillation (with an ICD case electrode as anode) and as an anode for bipolar sensing with the second, smaller conductor 212 as cathode. Thus, in one implementation, the exemplary patch 104 performs two functions as needed, sensing and defibrillating, each using a separate electrode.

Figure 7:
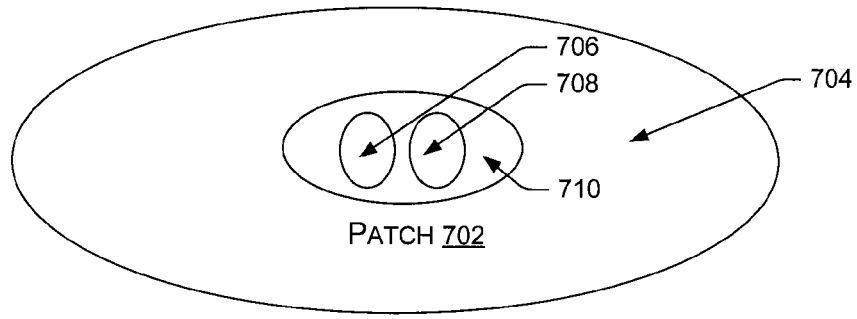
FIG. 7 is a diagram illustrating an exemplary dual electrode subcutaneous patch in which a sensing electrode is bipolar.

FIG. 7 shows another implementation of an exemplary patch 702, in which a relatively large electrode 704 is insulated from two smaller electrodes 706 and 708 that are in turn insulated from each other, e.g., by a region of electrical insulation 710. In this case, the two smaller electrodes 706 and 708 may act as bipolar sensing electrodes while the large electrode 704 acts as a defibrillation electrode. The two bipolar electrodes 706 and 708 may sense ventricular tachycardia and/or ventricular fibrillation, but in some implementation may also sense a patient's ongoing cardiac rhythm for purposes of pacing the heart.

Figure 8:
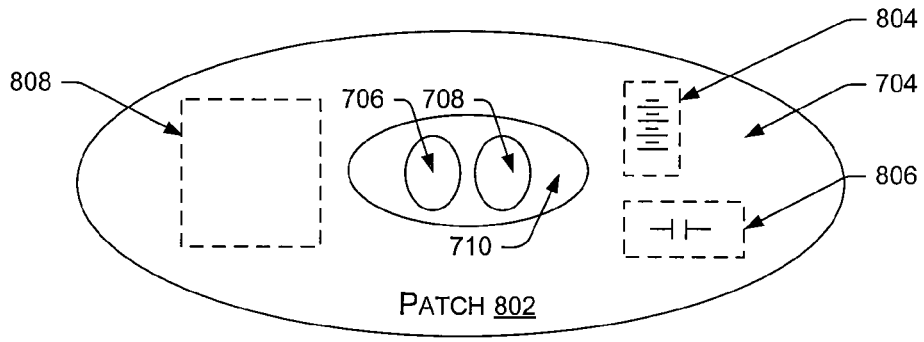
FIG. 8 is a diagram illustrating an exemplary subcutaneous patch with advanced onboard components.

FIG. 8 shows yet another implementation of an exemplary patch 802 that includes additional components inside the patch or on a non-cardiac facing side of the patch. For example, the exemplary patch 802 may include a battery 804, a capacitor 806, and a patch header 808. As described more fully below with respect to FIGS. 10-11, the patch header 808 may contain control circuitry; communications circuitry for communicating with an ICD 102 or external telemetry transceiver; a programmable microprocessor and memory for computing functions; a charging circuit for the capacitor; etc. Thus, the exemplary patch 802 may be programmable and capable of intelligent operation and decision-making. If the battery 804 is rechargeable, the patch 802 may include an induction coil for recharging the patch battery, the induction facilitated by the subcutaneous character of the patch 802 and its potential proximity to the surface of the body where a recharger can be stationed. If a communication wire 302 is used between the patch 802 and an ICD 102, then an induction coil in the patch 802 may also recharge a rechargeable ICD battery that is remote from the patch 802.

Exemplary ICD

Figure 9:
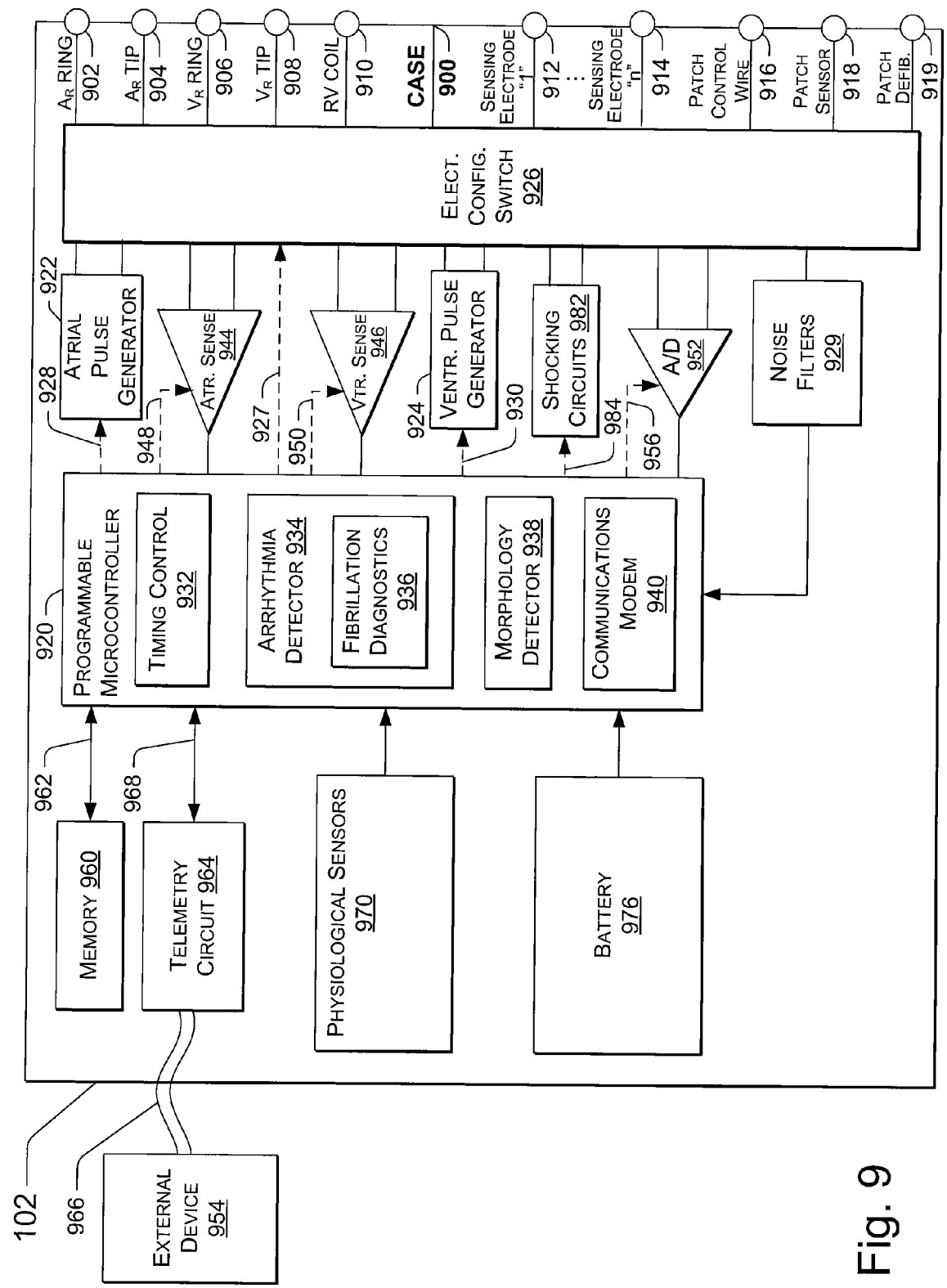
FIG. 9 is a block diagram of an exemplary subcutaneous implantable cardiac device.

FIG. 9 shows an exemplary implementation of an ICD 102 as described above. Such an ICD 102 can be characterized as a miniature computing device that is implanted subcutaneously into a body to monitor, pace, and correct a person's heart rhythm and other features of the person's cardiac cycle, and sometimes provide monitoring and therapy for other cardiovascular and bodily activities.

The block diagram of FIG. 9 depicts various components of an exemplary ICD 102. The illustrated ICD 102 is only presented as one example ICD 102 that could be used with the subject matter. Accordingly, the illustrated ICD 102 may contain more components than would be used in any one implementation of an ICD 102 for an exemplary system 100.

The components are typically contained in a case 900, which is often referred to as the "can", "housing", "encasing", or "case electrode", and may be programmably selected to act as the return electrode for unipolar operational modes. The case 900 may further be used as a return electrode alone or in combination with one or more of the proximal sensors (e.g., 304) and/or patch sensors (e.g., 706, 708). The case 900 further includes a connector (not shown) having a plurality of terminals shown schematically with the names of the electrodes or leads to which they are connected shown next to the terminals, including, in various implementations:

a right atrial ring terminal (AR RING) 902 for atrial ring electrode 406;
a right atrial tip terminal (AR TIP) 904 for atrial tip electrode 404;
a right ventricular ring terminal (VR RING) 906 for a right ventricular ring electrode (not shown);
a right ventricular tip terminal (VR TIP) 908 for a right ventricular tip electrode (not shown);
a right ventricular shocking terminal (RV COIL) 910 for an RV coil electrode (not shown);
one or more sensor terminals (e.g., 912 . . . 914) for one or more proximal sensors disposed on an ICD 102, an ICD header 103, an ICD antenna 303, and/or a communication wire 302; and
a patch control terminal 916 for a communication wire 302;
a patch sensor terminal 918 for a sensor (e.g., 706) positioned on a patch 104; and
a patch defibrillation terminal 919 for defibrillation energy to be transferred to a patch 104 via a communication wire 302.

An exemplary ICD 102 may include a programmable microcontroller 920 that controls various operations of the ICD 102, including cardiac monitoring and pacing therapy. Microcontroller 920 includes a microprocessor (or equivalent control circuitry), RAM and/or ROM memory, logic and timing circuitry, state machine circuitry, and I/O circuitry.

Exemplary ICD 102 further includes an atrial pulse generator 922 and a ventricular pulse generator 924 that generate pacing stimulation pulses e.g., for delivery by the right atrial lead 402, or other pacing modality via an electrode configuration switch 926. The electrode configuration switch 926 may include multiple switches for connecting the desired electrodes to the appropriate I/O circuits, thereby providing complete electrode programmability. Accordingly, switch 926, in response to a control signal 927 from the microcontroller 920, determines the polarity of the stimulation pulses (e.g., unipolar, bipolar, etc.) by selectively closing the appropriate combination of switches.

To provide possible stimulation therapy in each of the four chambers of the heart, the atrial and ventricular pulse generators 922 and 924 may include dedicated, independent pulse generators, multiplexed pulse generators, or shared pulse generators. The pulse generators 922 and 924 are controlled by the microcontroller 920 via appropriate control signals 928 and 930, respectively, to trigger or inhibit the stimulation pulses.

Microcontroller 920 is illustrated as including timing control circuitry 932 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 920 may also implement an arrhythmia detector 943. The arrhythmia detector 934 includes fibrillation diagnostics 936 for analyzing the patient's heart rates and rhythms and determining, based on this analysis, whether the patient is experiencing fibrillation or impending fibrillation. The fibrillation diagnostics 936 may also diagnose ventricular tachycardia. In one implementation, the data used to determine whether fibrillation is present is sensed by sensors on a patch 104 and communicated to the ICD 102 for analysis by the arrhythmia detector 234. In other implementations, however, the patch 104 may include a header 808 with computing capability and fibrillation diagnostics 936 onboard the patch 104. Parameters from other sensors located in an exemplary system 100 may also be considered, such as input from a morphology detector 938 to analyze wave shapes that occur during a patient's cardiac cycle and detect morphological-related parameters. If fibrillation is detected, the fibrillation diagnostics 936 provide instructions to direct defibrillation shocks to be administered through an electrode on the patch 104.

An exemplary ICD 102 can be equipped with a communication module in the form of modem (modulator/demodulator) 940 to enable communication, such as wireless communication, with an exemplary patch 104. The communication modem 940 may transmit sensing, pacing, and defibrillation instructions to the patch 104.

In one implementation, the communication modem 940 uses high frequency modulation. As one example, the modem 940 may transmit signals between a pair of electrodes of a cardiac lead, such as between the case 900 of the ICD 102 and a right ventricular tip electrode. The signals are transmitted in a high frequency range of approximately 20-80 kHz, as such signals travel through the body tissue in fluids without stimulating the heart or being felt by the patient. In another implementation, the communication modem uses an antenna 303.

The communication modem 940 may be implemented in hardware as part of the microcontroller 920, or as software/firmware instructions programmed into and executed by the microcontroller 920. Alternatively, the modem 940 may reside separately from the microcontroller as a standalone component.

The components 932, 934, 936, 938, 940 may also be implemented in hardware as part of the microcontroller 920, or as software/firmware instructions programmed into an implementation of the ICD 102 and executed on the microcontroller 920 during certain modes of operation. Although not shown, the microcontroller 920 may further include other dedicated circuitry and/or firmware/software components that assist in monitoring various conditions of the patient's heart and managing pacing therapies.

Atrial sensing circuits 944 may be selectively coupled to a right atrial lead 402 and/or to other sensors not in contact with cardiac tissue, such as sensors 304, 306, 308, 310, 312, and 314, etc. Ventricular sensing circuits 946 may be selectively coupled to a right ventricular lead and/or to other sensors not in contact with cardiac tissue, such as electrodes 204, 212, 316, 706, 708, etc. The sensing circuits 944 and 946 may include dedicated sense amplifiers, multiplexed amplifiers, or shared amplifiers. Switch 926 determines the "sensing polarity" of the cardiac signal by selectively closing the appropriate switches. In this way, a clinician may program the sensing polarity independent of the stimulation polarity.

Each sensing circuit 944 and 946 may employ one or more low power precision amplifiers with programmable gain and/or automatic gain control, bandpass filtering, and a threshold detection circuit to selectively sense the cardiac signal of interest. The automatic gain control enables the exemplary ICD 102 to sense low amplitude signal characteristics of atrial or ventricular fibrillation. The ICD 102 may also include additional noise filters 929 to improve sensing signals from sensors that may not be in contact with cardiac tissue. The additional noise filters 929 may include EMI filters and filters for discarding extraneously sensed depolarization signals.

The outputs of the atrial and ventricular sensing circuits 944 and 946 are connected to the microcontroller 920 that, in turn, is able to trigger or inhibit the atrial and ventricular pulse generators 922 and 924 in a demand fashion in response to the absence or presence of cardiac activity in the appropriate chambers of the heart. The sensing circuits 944 and 946 receive control signals from the microcontroller 920 over signal lines 948 and 950 to control, for example, the gain and/or threshold of polarization charge removal circuitry (not shown) and the timing of blocking circuitry (not shown) optionally coupled to the inputs of the sensing circuits 944, 946.

Cardiac signals may be supplied to an analog-to-digital (ND) data acquisition system 952, which is configured to acquire intracardiac electrogram signals, convert the raw analog data into a digital signal, and store the digital signals for later processing and/or telemetric transmission to an external device 954. The data acquisition system 952 may be coupled to a right atrial lead 402, other cardiac leads, and sensors not in contact with cardiac tissue (e.g., 204, 212, 304, 306, 308, 310, 312, 314, 316, etc.) through the switch 926 to sample cardiac signals across any pair of desired electrodes.

The data acquisition system 952 is coupled to the microcontroller 920, or other detection circuitry, to assist in detecting an evoked response from the heart 106 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 920 detects a depolarization signal during a window following a stimulation pulse, the presence of which indicates that capture has occurred. The microcontroller 920 enables capture detection by triggering the ventricular pulse generator 924 to generate a stimulation pulse, starting a capture detection window using the timing control circuitry 932 within the microcontroller 920, and enabling the data acquisition system 952 via control signal 956 to sample the cardiac signal that falls in the capture detection window and, based on the amplitude, determines if capture has occurred.

The microcontroller 920 is further coupled to a memory 960 by a suitable data/address bus 962. The programmable operating parameters used by the microcontroller 920 are stored in memory 960 and used to customize the operation of the exemplary ICD 102 to suit the needs of a particular patient. Such operating parameters define, for example, pacing pulse amplitude, pulse duration, electrode polarity, rate, sensitivity, automatic features, arrhythmia and fibrillation detection criteria, and the amplitude, waveshape and vector of each shocking pulse to be delivered to the patient's heart 106 within each respective tier of therapy.

The operating parameters of the exemplary ICD 102 may be non-invasively programmed into the memory 960 through a telemetry circuit 964 in telemetric communication via communication link 966 with the external device 954, such as a programmer, local transceiver, or a diagnostic system analyzer. The microcontroller 920 can activate the telemetry circuit 964 with a control signal 968. The telemetry circuit 964 allows intracardiac electrograms and status information relating to the operation of the exemplary ICD 102 (as contained in the microcontroller 920 or memory 960) to be sent to the external device 954 through an established communication link 966.

The physiological sensors 970 referred to above can further include, for example, "rate-responsive" sensors that adjust pacing stimulation rates according to the exercise state of the patient. Accordingly, the microcontroller 920 responds by adjusting the various pacing parameters (such as rate, AV Delay, V-V Delay, etc.) at which the atrial and ventricular pulse generators 922 and 924 generate stimulation pulses.

The physiological sensors 970 may include mechanisms and sensors to detect bodily movement, changes in cardiac output, changes in the physiological condition of the heart, diurnal changes in activity (e.g., detecting sleep and wake states), G-force acceleration of the pacemaker case 900, length of the cardiac QT interval, blood oxygen saturation, blood pH, changes in blood pressure, changes in temperature, respiration rate, and QRS wave duration. While shown as being included within the exemplary ICD 102, the physiological sensor(s) 970 may also be external to the exemplary ICD 102, yet still be implanted within or carried by the patient, e.g., a blood pressure probe. Examples of physiological sensors external to the case 900 that may be deployed by an ICD 102 include sensors that, for example, sense respiration activities, $O_2$ saturation, evoked response, pH of blood, and so forth.

The illustrated physiological sensors 970 may include one or more activity/position sensors (e.g., 1D or 3D accelerometers, movement sensors, etc.) to detect changes in the patient's position.

In one configuration, accelerometer output signal is band-pass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state. The activity variance can be monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which is hereby incorporated by reference.

A minute ventilation (MV) sensor may also be included in the physiological sensors 470 in order to sense rate and depth of breathing. Minute ventilation can be measured as the total volume of air that moves in and out of a patient's lungs in a minute. The MV sensor may use transthoracic impedance, which is a measure of impedance across the chest cavity, to sense air movement.

An exemplary ICD 102 additionally includes a battery 976 that provides operating power to all of the components shown in FIG. 9. The battery 976 is capable of operating at low current drains for long periods of time (e.g., less than 10 μA), and is capable of providing high-current pulses (for capacitor charging) when the patient requires a shock pulse (e.g., in excess of 2 A, at voltages above 2 V, for periods of 10 seconds or more). The battery 976 also desirably has predictable discharge characteristics so that elective replacement time can be detected. As one example, the exemplary ICD 102 employs lithium/silver vanadium oxide batteries.

The exemplary ICD 102 can further include magnet detection circuitry (not shown), coupled to the microcontroller 920, to detect when a magnet is placed over the exemplary ICD 102. A magnet may be used by a clinician to perform various test functions of the exemplary ICD 102 and/or to signal the microcontroller 920 that an external programmer (e.g., 954) is in place to receive or transmit data to the microcontroller 920 through the telemetry circuits 964.

The exemplary ICD 102 may be operated as a subcutaneous cardioverter/defibrillator, which detects the occurrence of an arrhythmia and automatically applies an appropriate electrical shock therapy via an electrode on the patch 104 or the coil electrodes 150 to the heart aimed at terminating the detected arrhythmia or fibrillation. To this end, the microcontroller 920 further controls a shocking circuit 982 via a control signal 984. The shocking circuit 982 generates shocking pulses of low (e.g., up to 0.5 joules), moderate (e.g., 0.5-10 joules), or high energy (e.g., 11 to 40 joules), as selected by the microcontroller 920. Such shocking pulses are applied to the patient's heart 106 through at least two shocking electrodes selected, for example, from an electrode 204 of a patch 104 and the case 900.

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 920 is capable of controlling the synchronous or asynchronous delivery of the shocking pulses.

More generally, the exemplary ICD 102 can be programmed to stimulate different sets of vascular and cardiac muscles through the same lead/electrode system. The exemplary ICD 102 can be programmed to vary the output voltage of various pulses to effectively stimulate different muscles of the heart and blood vessels, even though the lead and electrode placement does not change.

Programmable Patch Array with Defibrillation Capability

Figure 10:
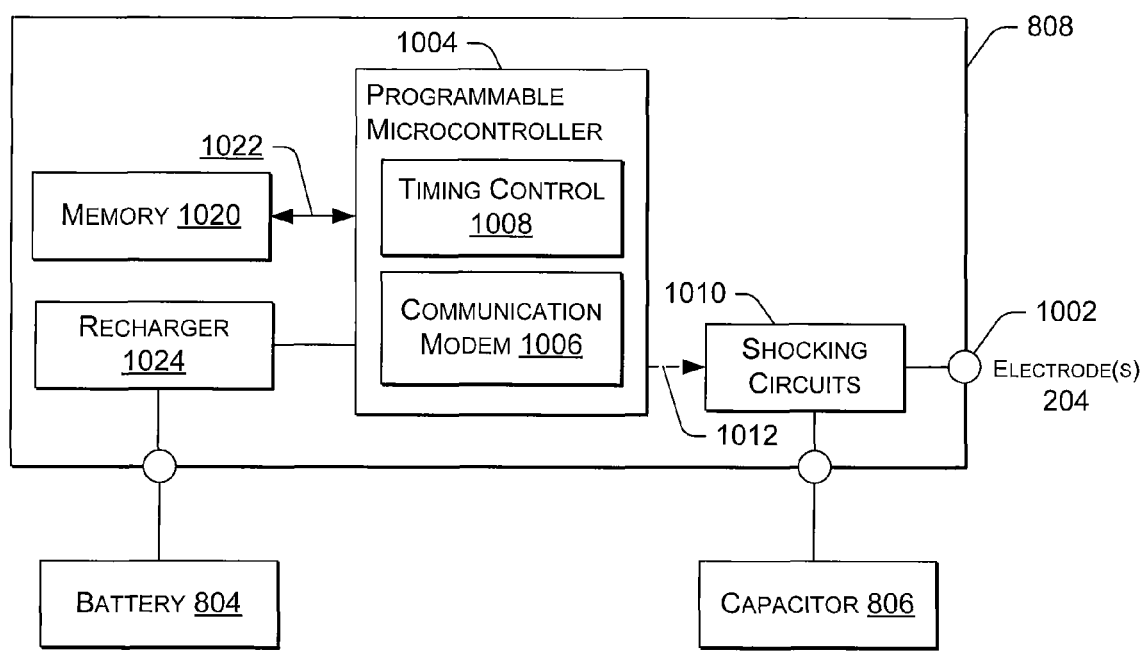
FIG. 10 is a block diagram of advanced components of an exemplary subcutaneous patch with onboard shock generating capability.

FIG. 10 shows one exemplary layout of components that can be included in a patch 802 in addition to patch electrodes, i.e., in order to create a patch array. The components can be included in a patch header 808, shown here in greater detail than in FIG. 8. The patch header 808 is shown in relation to an onboard battery 804 and an onboard capacitor 806. In some implementations the capacitor 806 can also included in the patch header 808.

In this example, the components of the illustrated patch header 808 render a patch (e.g., 802) into a relatively passive unit that applies defibrillation shocks in response to commands from the ICD 102. Such a patch header 808 includes a programmable microcontroller 1004 to control the defibrillation operation of the patch 802. A communication modem 1006 is provided to facilitate communication, such as wireless communication, with the ICD 102. The communication modem 1006 may be implemented in hardware as part of the microcontroller 1004, or as software/firmware instructions programmed into and executed by the microcontroller 1004. Alternatively, the modem 1006 may reside separately from the microcontroller 1004 as a standalone component. In its simplest form, the communication modem 1006 may be configured as a uni-directional receiver to receive communication from the ICD 102. The illustrated patch header 808 allows the patch 802 to generate its own shocking currents, instead of just conducting a defibrillation current received from the ICD 102. The onboard battery 804 may also balance the mass of an exemplary subcutaneous system 100 so that the ICD 102 can be made smaller and does not have to include a bulky battery for generating defibrillation currents.

The onboard microcontroller 1004 may be further equipped with timing control circuitry 1008 to control timing of the stimulation pulses being applied to the left ventricle in response to command signals received via communication modem 306 from the ICD 102.

The patch header 808 may include shocking circuits 1010 to generate defibrillation pulses for delivery by the electrode 704. The shocking circuits 1010 are controlled by the microcontroller 1004 via control signal 1012. The patch header 808 may have a defibrillation electrode terminal 1002 for connecting with a defibrillation electrode 704.

The microcontroller 1004 is coupled to a memory 1020 via data/address bus 1022. Any programmable operating parameters to be used by the microcontroller 1004 can be stored in memory 1020 and used to customize the operation of the patch 802 to suit the needs of a particular patient. Such operating parameters can be programmed into the memory 1020 via instructions transmitted from the ICD 102 to the patch 802, where they are received at the communication modem 1006 and stored in the memory 1020. In simpler constructions, where no programmable operating parameters are employed or desired, the memory 1020 and bus 1022 may be omitted.

The battery 804 supplies operating power to all of the components shown in FIG. 10. The battery 804 is capable of operating at low current drains for long periods of time (e.g., less than 10 µA), and is capable of providing sufficient voltage and current to charge the capacitor 806 for applying defibrillation to the heart 106. As one example, the battery 804 is implemented as one or more lithium/silver vanadium oxide batteries.

In the FIG. 10 configuration, the patch 802 delivers defibrillation pulse(s) to the patient's heart, e.g., left ventricle, in response to commands transmitted from the ICD 102. The commands are communicated to the communication modem 1006. The commands are processed by the microcontroller 1004. Once received and processed, the patch 802 responds by generating a defibrillation pulse at the shocking circuits 1010 delivering the pulse(s) via the electrode(s) 704. The pulse may be applied immediately, or after some timing delayed dictated by the timing control circuitry 1008.

If the battery 804 is rechargeable, the patch 802 may include recharging circuitry 1024 (e.g., an induction coil and diode; charge tapering circuitry; etc.) for recharging the battery 804. Recharging the battery 804 via induction from an external charger is facilitated by the subcutaneous character of the patch 802, which allows a close proximity to the external charger.

Programmable Patch Array with Defibrillation and Sensing Capabilities

Figure 11:
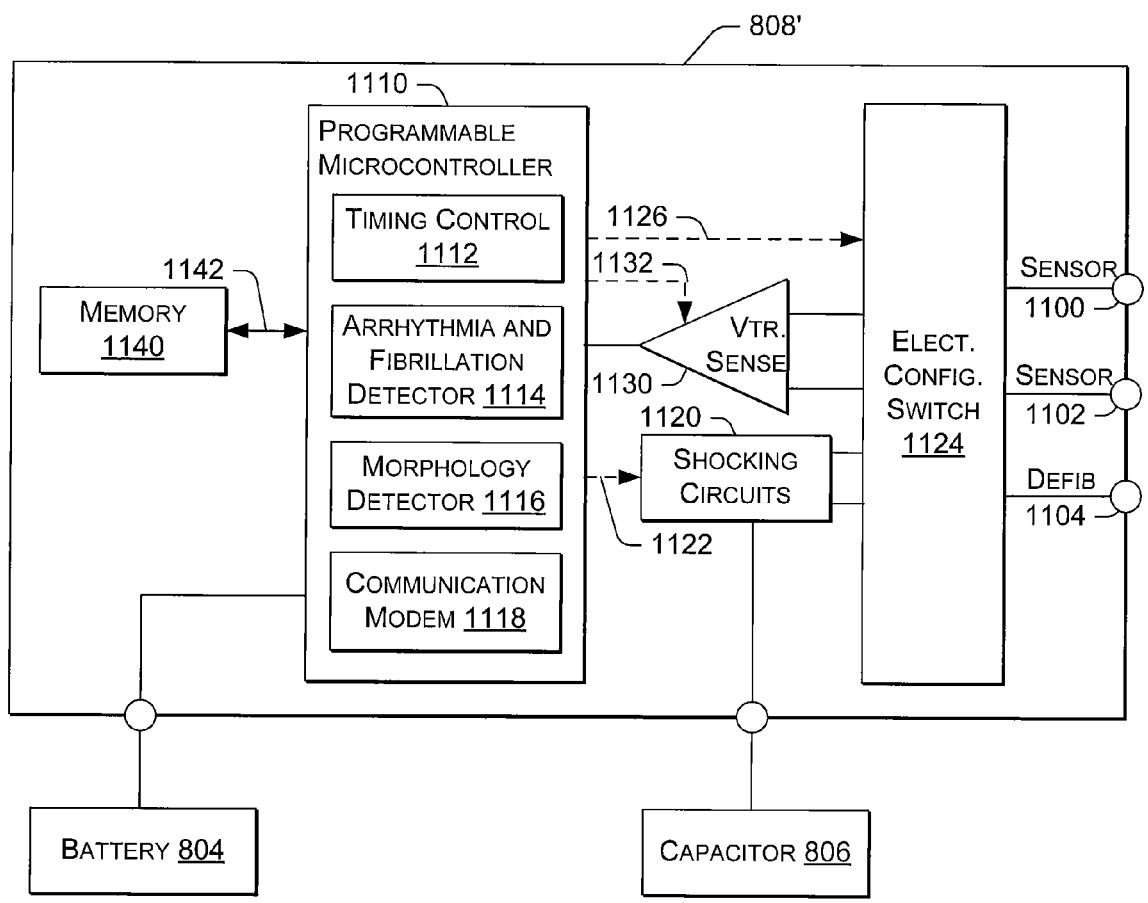
FIG. 11 is a block diagram of advanced components of an exemplary subcutaneous patch with onboard shock generating and sensing capabilities.

FIG. 11 shows another exemplary layout of components that can be included in a patch 802' in addition to patch electrodes, i.e., in order to create a patch array. The components can be included in a patch header 808'. The patch header 808' is shown in relation to an onboard battery 804 and an onboard capacitor 806. In some implementations the capacitor 806 can also included in the patch header 808.

The components of the patch header 808' render more functionality to a patch 802' than those components shown in FIG. 10. In this example, the patch header 808' is configured with sensing capabilities and diagnostic detection capabilities, making the host patch 802' more self-contained (more like the internal components of the ICD 102 itself). The patch header 808' may have a connector (not shown) with a plurality of terminals for connecting to associated electrodes. The terminals may include a first sensor electrode terminal 1100, a second sensor electrode terminal 1102, and a defibrillation electrode terminal 1104. More or less electrodes may be used in other configurations. It should be noted that in one implementation, the multiple terminals (1100, 1102, 1104) for connecting to electrodes may all connect to the same electrode, to be used for different sensing and shocking functions. Thus, control logic stored in memory 1140 and implemented in the microcontroller 1110 may dictate whether the current operation of an electrode 204 is to be for sensing or for shocking. Similarly, the multiple terminals may be combined into one terminal if a single electrode 204 is to be used for multiple functions. Sensor terminals (e.g., 1100 and 1102) may also connect to different electrodes of a single bipolar sensor.

The patch header 808' includes a programmable microcontroller 1110 that controls various operations of the patch 802', and thus includes an arrhythmia and fibrillation detector 1114 and a morphology detector 1116. Timing control circuitry 1112 may be configured to control the timing of the defibrillation pulses applied via one or more electrodes, e.g., 704. The timing may be integrated with timing stipulated by the logic in the ICD 102. Microcontroller 410 has an arrhythmia and fibrillation detector 1114 for detecting cardiac events and a morphology detector 1116 for detecting morphological-related parameters.

The patch header 808' is further equipped with a communication modem 1118 to facilitate communication, such as wireless communication, with the ICD 102. The communication modem 1118 may be configured as a unidirectional receiver to receive communication from the ICD 102 or as a bi-directional transceiver that is capable of both reception and transmission.

The patch header 808' may further include shocking circuits 1120 to generate defibrillation pulses for delivery an electrode 704. The shocking circuits 1120 are controlled by the microcontroller 1110 via control signal 1122 and are coupled to the electrode or lead terminals 1100, 1102, 1104 via an electrode configuration switch 1124. The switch 1124 connects desired electrodes to the appropriate I/O circuits, thereby providing electrode programmability. The microcontroller 1110 controls the switch 1124 via a control signal 1126.

In the illustrated implementation, the patch header 808' is equipped with ventricular (VTR. SENSE) sensing circuit 1130, which can be selectively coupled to electrodes to detect the cardiac activity in the left ventricle of the heart 106 or at the apex 110 of the heart 106, including tachycardia and fibrillation. The ventricular sensing circuit 1130 may include dedicated sense amplifiers, multiplexed amplifiers, or shared amplifiers. It may employ one or more low power precision amplifiers with programmable gain and/or automatic gain control, bandpass filtering, and a threshold detection circuit, to selectively sense the cardiac signal of interest. The ventricular sensing circuit 1130 is controlled by the microcontroller 1110 via control signal 1132.

The microcontroller 1110 is coupled to a memory 1140 via data/address bus 1142 to store various programmable operating parameters used to customize operation of the patch 802'. Operating parameters can be programmed into the memory 1140 via instructions transmitted from the ICD 102 to the patch 802', where they are received at the communication modem 1118 and stored in the memory 1140. The patch 802' may also have a battery 804 to provide power to all components in the patch 802'. The battery 804 also provides power to the capacitor 806 for the defibrillation pulses.

In the FIG. 11 configuration, the patch 802' can deliver defibrillation pulses to the patient's heart 106 in response to commands transmitted from the ICD 102. This is similar to the patch 802 of FIG. 10. Such commands are communicated to the communication modem 1118. Once received, the patch 802' responds by generating one or more defibrillation shocks at the shocking circuits 1120 and delivering the shocks via an electrode(s), e.g., 704.

Additionally, the patch 802' can be configured to sense heart activity, including fibrillation and high heart rates indicative of tachycardia. The arrhythmia and fibrillation detector 1114 may make a preliminary assessment of a cardiac event. In one implementation, this data and/or assessment are transmitted via the communication modem 1118 to the ICD 102 for evaluation. There, the arrhythmia detector 934 and fibrillation diagnostics 936 in the ICD 102 discern whether the cardiac event is ventricular tachycardia or ventricular fibrillation. If the ICD 102 determines that the patient is experiencing either ventricular tachycardia or ventricular fibrillation, the ICD 102 transmits commands back to the patch 802'. Upon receipt, the patch 802' generates cardioversion shocks, or defibrillation shocks to treat the respective condition.

In an alternative implementation, the arrhythmia and fibrillation detector 1114 of the patch 802' makes its own diagnosis of whether fibrillation is occurring and generates defibrillation shocks accordingly. Thus, sensing, diagnosing, and treating fibrillation occur onboard the patch without intervention of the ICD 102.

In yet another implementation, either the ICD 102 or the patch 802' make a tentative diagnosis of fibrillation and a proximal sensor in physical contact with cardiac tissue, such as an electrode of a right atrial lead 402, confirms the tentative fibrillation diagnosis before applying a defibrillation shock through the patch 802'.

Exemplary Methods

Figure 12:
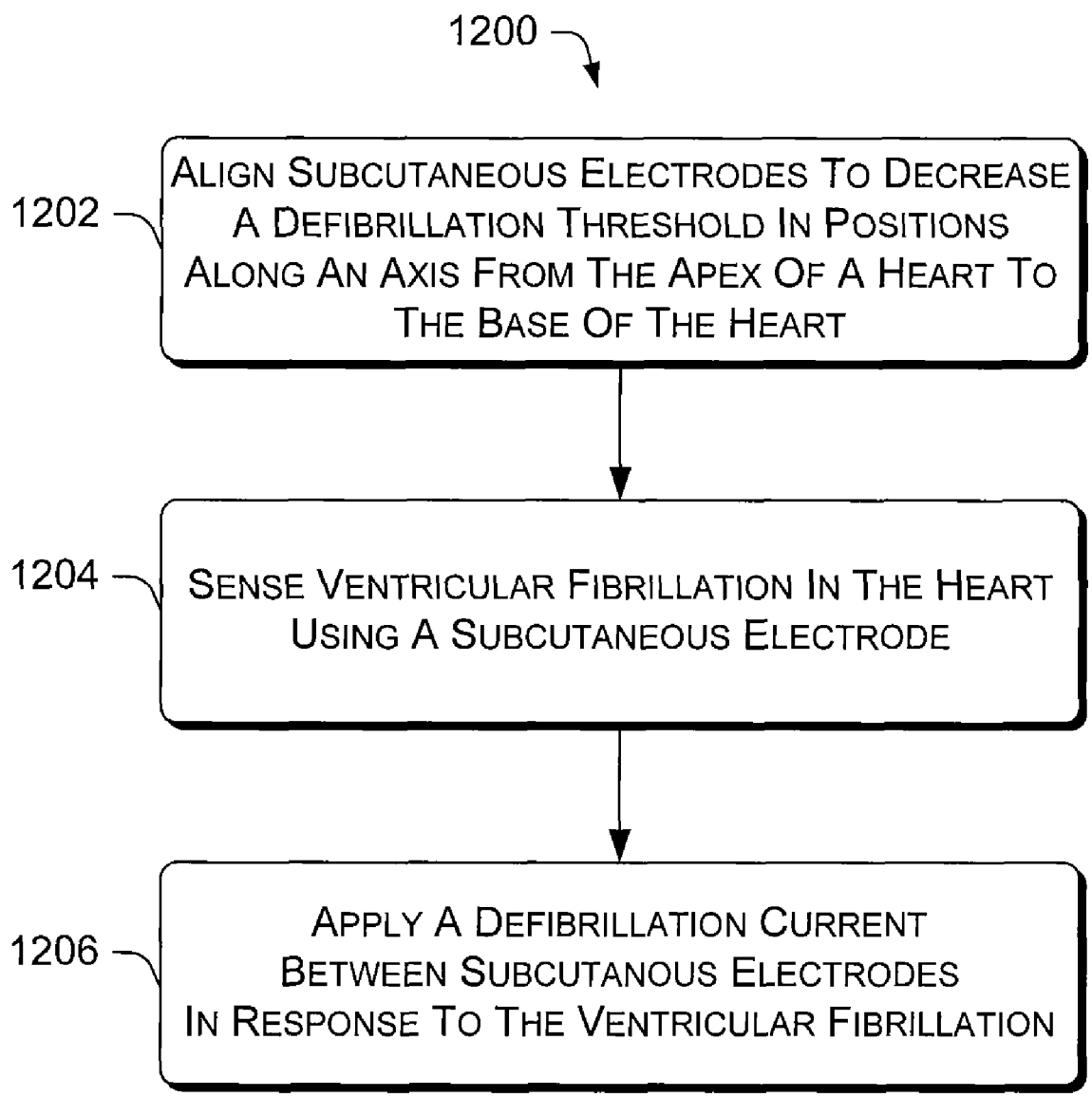
FIG. 12 is a flow diagram of an exemplary method of treating ventricular fibrillation at a lowered defibrillation threshold using an exemplary subcutaneous system.

FIG. 12 shows an exemplary method 1200 of decreasing a defibrillation threshold using an exemplary subcutaneous system. This method 1200 may be implemented in connection with any suitably configured subcutaneous device, although it will be described as being executed by the exemplary implantable device 102 of FIG. 7 and patch 802 of FIG. 8. In the flow diagram of FIG. 12, the operations are summarized in individual blocks. Some operations may be performed in hardware and/or as machine-readable instructions (software or firmware) that can be executed by a processor, such as microcontrollers 920, 1004, 1110, etc.

At block 1202, subcutaneous electrodes are aligned to decrease a defibrillation threshold in positions along an axis from the apex of a heart to the base of the heart. The axis formed by a line between the apex of the heart and the heart's base may include natural conduction pathways or electrical vectors that depolarization waves follow when the ventricles are being stimulated by the heart's own electrical system. Thus, aligning subcutaneous electrodes for defibrillation along this general axis lowers the defibrillation threshold. The alignment of electrodes along such a ventricular axis may be implemented during installation of the electrodes of an exemplary implantable system 100, but alignment may also be implemented logically, by logically selecting electrodes that lie along a desirable ventricular axis from out of an array of electrodes, some of which may not lie along the desirable ventricular axis.

The geometry, composition, and surface area of an electrode may also lower the effective defibrillation threshold. For example, a defibrillation electrode with a surface area that is significantly larger than conventional defibrillation electrodes may avoid ionic polarizations that build up in the vicinity of conventional small surface area electrodes and that raise the defibrillation threshold for the conventional electrodes.

At block 1204, ventricular fibrillation is sensed, for example, by a subcutaneous electrode. When a subcutaneous electrode senses fibrillation, the signal may not always be as reliable as a signal from an electrode in direct physical contact with the heart. A subcutaneous sensing electrode is typically further away from the electrical activity being sensed than a conventional electrode in contact with cardiac tissue. Thus, in one implementation, amplifiers for subcutaneous sensing electrodes may have more gain, and more noise filtering may be used on signals from a subcutaneous electrode.

Because implementations of an exemplary subcutaneous system may have components arranged in different parts of the thoracic cavity, there can be a variety of locations where a subcutaneous electrode may be positioned. Multiple sensors may even be used in an array to sense fibrillation. The variety of possible locations provides the advantage of being able to select a sensor location near an electrical feature of the heart. For example, an electrode on a subcutaneous patch can be situated near the apex of the heart, while a sensor positioned along a communication wire between the patch and an ICD may be positioned near the SA or AV node of the heart.

At block 1206, a defibrillation current is applied between two subcutaneous electrodes to treat the ventricular fibrillation. The defibrillation current can be generated in a subcutaneous ICD and transferred to a patch electrode at the apex of the heart via a wire. The patch electrode applies the current across the heart along the above-described axis to a second subcutaneous electrode, for example on the case or header of the subcutaneous ICD. Control of the defibrillation shocks may be performed by electronics in the ICD or in the patch. In one implementation of the subcutaneous patch, the battery and capacitor for generating a defibrillation shock are located onboard the patch. In the same or another implementation of a subcutaneous patch, a microprocessor onboard the patch executes instructions to analyze sensing data and decide whether ventricular fibrillation is occurring. The instruction may then govern the parameters for delivering a defibrillation shock.

Figure 13:
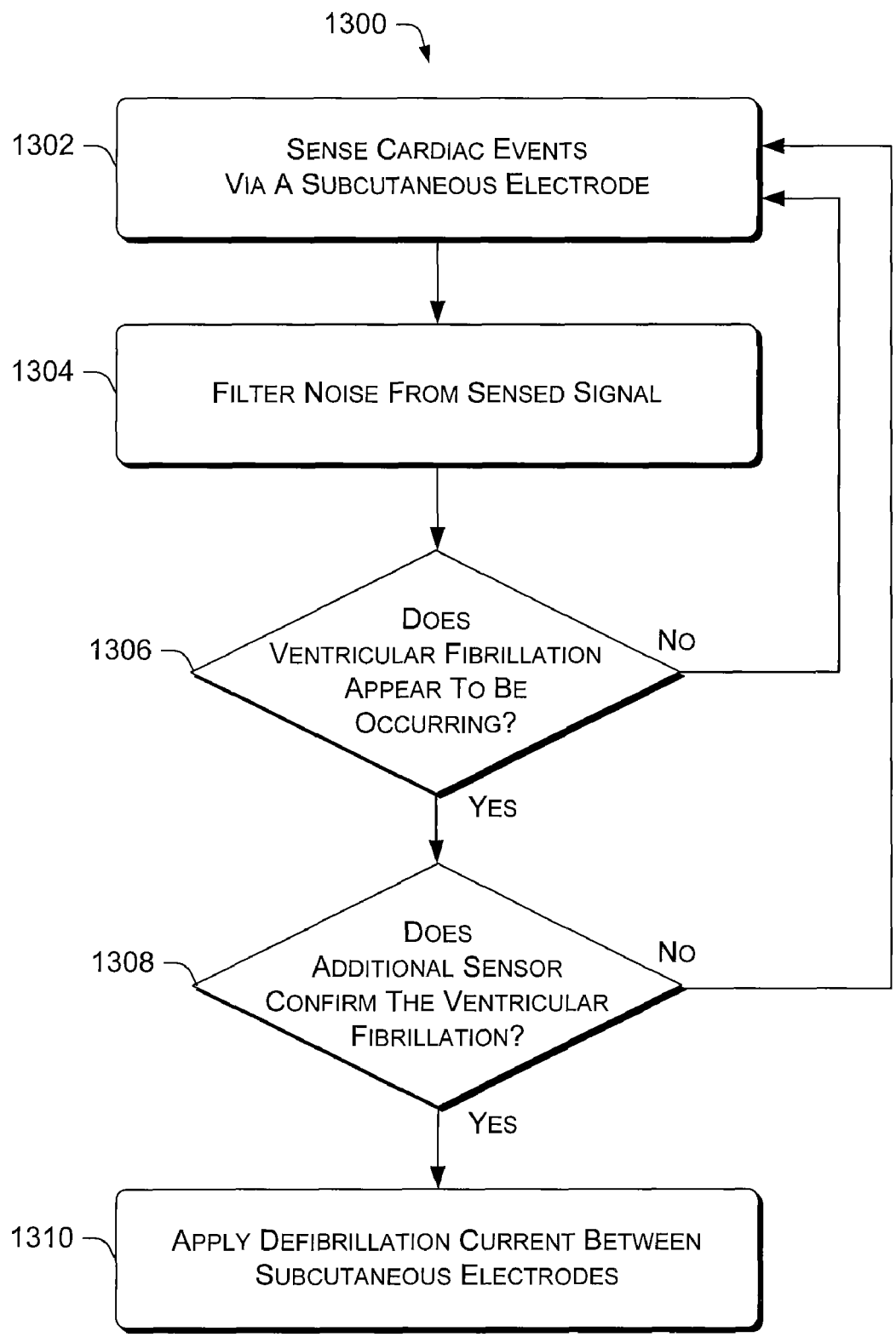
FIG. 13 is a flow diagram of an exemplary method of sensing ventricular fibrillation using one or more subcutaneous sensors.

FIG. 13 shows an exemplary method 1300 of sensing ventricular fibrillation using one or more subcutaneous sensors and treating the fibrillation sensed. The exemplary method 1300 may be implemented in connection with any suitably configured subcutaneous device, although it will be described as being executed by the exemplary implantable device 102 of FIG. 7 and patch 802 of FIG. 8, as configured in FIG. 4, for example. In the flow diagram of FIG. 13, the operations are summarized in individual blocks. Some operations may be performed in hardware and/or as machine-readable instructions (software or firmware) that can be executed by a processor, such as microcontrollers 920, 1004, 1110, etc.

At block 1302, cardiac events are sensed via a subcutaneous electrode. This electrode may be located on a subcutaneous patch placed anteriorly over (superficial to) the apex of a patient's heart or may be located in many other subcutaneous locations. For example, the sensor can be located on the exterior of a subcutaneous ICD, or along a wire that connects such an ICD with the aforementioned patch. Typically a sensor is located near a native source of electrical activity in the heart, such as the SA node. The sensor may be bipolar or unipolar.

Because a subcutaneous sensor does not have the advantage of being in direct physical contact with the heart, it is prone to more extraneous noise and sometimes weaker signal reception than electrodes positioned on a conventional endocardial lead that contacts cardiac tissue.

At block 1304, noise is filtered from the signal of the sensed cardiac events. Usually the noise consists of extraneous electromagnetic interference (EMI) and unwanted reception of depolarization waves from a broader area of the heart than desired. Whereas an electrode in contact with cardiac tissue can more easily pinpoint a signal as it occurs at the place of contact, a subcutaneous electrode may receive signals from several parts of the heart at once. The noise filtering may be built into atrial and ventricular sensing components, such as components 944, 946, 1132, but may also be added as discreet noise filters 929 tuned to filter out noise that subcutaneous electrodes are especially prone to, or tuned to filter out noise particular to a specific electrode.

At block 1306, the system determines if ventricular fibrillation is likely occurring. If the condition is not likely occurring (i.e., the "no" branch from block 1306), the method 1300 branches back to block 1302 to sense cardiac events. However, if fibrillation is likely occurring (i.e., the "yes" branch from block 1306), the system determines whether a second sensor confirms ventricular fibrillation (block 1308). In one implementation, such as that shown in FIG. 4, the second sensor is an electrode in contact with cardiac tissue. Since applying a defibrillation pulse is a relatively serious step, the exemplary method 1300 double-checks the tentative diagnosis of fibrillation made by a subcutaneous sensor at block 1306.

If the additional sensor does not confirm that ventricular fibrillation is occurring (i.e., the "no" branch from block 1308), the exemplary method 1300 continues to sense cardiac events via the subcutaneous electrode (block 1302). Conversely, if the additional sensor confirms that fibrillation is occurring (i.e., the "yes" branch from block 1308), the system applies a defibrillation shock between subcutaneous electrodes (block 1310) in an effort to halt the confirmed ventricular fibrillation.

For each shock delivered, the exemplary method 1300 can start anew. That is, a subcutaneous sensor detects whether ventricular fibrillation is occurring (block 1302). Noise is filtered (block 1304), and the test at block 1308 is reapplied. In an alternative implementation, once a defibrillation shock has been delivered between subcutaneous electrodes, feedback about whether fibrillation is still occurring is gathered directly from a sensor in contact with cardiac tissue, if available. It should be pointed out that in one implementation the exemplary method 1300 can be performed entirely by subcutaneous components. The exemplary method 1300 can proceed directly to application of defibrillation pulses based only on feedback from subcutaneous sensors. The input from a non-subcutaneous component in direct contact with cardiac tissue is only used in implementations in which such an electrode in contact with cardiac tissue is available.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. An implantable system, comprising:
   a defibrillator device subcutaneously implantable superficial to a left atrium of a heart wherein the defibrillator device comprises control logic configured to detect for ventricular fibrillation based on sensed cardiac activity;
   a patch device subcutaneously implantable superficial to an apex of the heart, wherein the patch device comprises control logic, wherein the patch device is communicatively coupled with the defibrillator device via a wireless communication link
   a subcutaneously implantable wire electrically coupling the defibrillation device with the patch device; and
   a sensor configured to sense cardiac activity, the sensor communicatively coupled with the defibrillator device through the wire such that sensed cardiac activity is received by the defibrillator device;
   wherein in response to the defibrillator device detecting ventricular fibrillation in the heart, the defibrillator device administers a defibrillation shock via the patch device.

2. The implantable system as recited in claim 1, wherein the sensor is positioned along the wire.

3. The implantable system as recited in claim 1, wherein the sensor is included in the patch device.

4. The implantable system as recited in claim 1, wherein the patch device includes an electrode that functions as the sensor and as a cathode for applying the defibrillation shock.

5. The implantable system as recited in claim 4, further comprising a circuit to switch between a sensing function of the electrode and a shocking function of the electrode.

6. The implantable system as recited in claim 1, wherein the patch device includes a first electrode comprising the sensor and a second electrode for applying the defibrillation shock.

7. The implantable system as recited in claim 1, wherein the patch device comprises one of a mesh electrode or a coil electrode.

8. The implantable system of claim 1 wherein:
   the defibrillator device is configured to generate a defibrillation current in response to detection of ventricular fibrillation and transfer the current through the wire to the patch device; and
   the patch device control logic is configured to apply the current between itself and a subcutaneously implantable electrode.

9. The implantable system of claim 8 wherein the subcutaneously implantable electrode is a part of the defibrillator device.

10. The implantable system of claim 1 wherein:
    the defibrillator device is configured to output a defibrillation command to the patch device though the wire, in response to detection of ventricular fibrillation; and
    the patch device comprises a battery and a capacitor for generating the defibrillation shock and the patch device control logic is configured to deliver the defibrillation shock in response to the defibrillation command.

11. The implantable system of claim 1 wherein:
    the patch device control logic is configured to detect for ventricular fibrillation based on sensed cardiac activity;
    the sensor is communicatively coupled with the patch device through the wire such that sensed cardiac activity is received by the patch device; and
    in response to the patch device detecting ventricular fibrillation in the heart, the patch device delivers a defibrillation shock.

12. The implantable system of claim 1 wherein:
    the patch device control logic is configured to detect for ventricular fibrillation based on sensed cardiac activity;
    the sensor is communicatively coupled with the patch device through the wire such that sensed cardiac activity is received by the patch device;
    in response to the patch device detecting ventricular fibrillation in the heart, the patch device transmits data corresponding to the sensed cardiac activity to the defibrillator device; and
    the defibrillator device control logic is configured to processes the data to discern whether the cardiac event is ventricular fibrillation or ventricular tachycardia.

13. The implantable system of claim 12 wherein:
    the defibrillator device is configured to transmit a cardioversion command to the patch device in response to ventricular tachycardia and a defibrillation command in response to ventricular fibrillation; and
    the patch device is configured to generate and deliver a cardioversion shock in response to a cardioversion command and a defibrillation shock in response to a defibrillation command.

14. The implantable system of claim 13 wherein commands are transmitted through the wire.

15. The implantable system of claim 13 wherein commands are transmitted wirelessly.

16. The implantable system of claim 1 further comprising an endocardially implantable electrode configured to sense cardiac activity from an endocardial location, the electrode electrically coupled to the defibrillator device, wherein:

the patch device control logic is configured to detect for ventricular fibrillation based on sensed cardiac activity;

the sensor is communicatively coupled with the patch device through the wire such that sensed cardiac activity is received by the patch device;

the defibrillator device control logic is configured to detect for ventricular fibrillation based on endocardially sensed cardiac activity; and in response to the patch device detecting ventricular fibrillation in the heart, the defibrillator device processes endocardially sensed cardiac activity to detect for fibrillation and thereby confirm the detection by the patch device.

\* \* \* \* \*